US007595370B2

(12) United States Patent
Plehiers et al.

(10) Patent No.: US 7,595,370 B2
(45) Date of Patent: *Sep. 29, 2009

(54) PROCESS FOR THE PREPARATION OF POLYORGANOSILYLATED CARBOXYLATE MONOMERS OR POLYMERS THEREOF

(75) Inventors: Mark Plehiers, Bruxelles (BE); Michel Gillard, Louvain-la-Neuve (BE)

(73) Assignee: PPG B.V., Uithoorn (NL)

( * ) Notice: Subject to any disclaimer, the term of this patent is extended or adjusted under 35 U.S.C. 154(b) by 469 days.

This patent is subject to a terminal disclaimer.

(21) Appl. No.: 10/520,636

(22) PCT Filed: Jul. 9, 2003

(86) PCT No.: PCT/EP03/07360

§ 371 (c)(1),
(2), (4) Date: Aug. 5, 2005

(87) PCT Pub. No.: WO2004/007591

PCT Pub. Date: Jan. 22, 2004

(65) Prior Publication Data

US 2006/0142516 A1    Jun. 29, 2006

(30) Foreign Application Priority Data

Jul. 10, 2002  (EP)  ................... 02254861
Aug. 8, 2002  (EP)  ................... 02255549

(51) Int. Cl.
*C08F 230/08*  (2006.01)
*C07F 7/04*   (2006.01)

(52) U.S. Cl. .................. 526/279; 526/319; 556/440; 556/442; 424/78.09

(58) Field of Classification Search ................ 526/279, 526/319; 556/440, 442; 424/78.09
See application file for complete search history.

(56) References Cited

U.S. PATENT DOCUMENTS

| 3,346,610 | A | * | 10/1967 | Omietanski et al. ......... 556/442 |
| 4,593,055 | A | | 6/1986 | Gitlitz et al. |
| 6,031,019 | A | * | 2/2000 | Tsutsumi et al. ............ 523/160 |
| 6,063,887 | A | * | 5/2000 | Okawa ....................... 528/23 |
| 6,172,132 | B1 | | 1/2001 | Nakamura et al. |

* cited by examiner

*Primary Examiner*—Robert D. Harlan
(74) *Attorney, Agent, or Firm*—Goodwin Procter LLP

(57) ABSTRACT

The present invention relates to a process for the preparation of polyorganosilylated carboxylate monomers or polymers thereof, comprising the steps of reacting a cyclosiloxane of formula (R4R5SiO)n with an unsaturated organosilylated carboxylate monomer or a copolymer or a polymer thereof under the presence of a suitable catalyst.

27 Claims, No Drawings

PROCESS FOR THE PREPARATION OF POLYORGANOSILYLATED CARBOXYLATE MONOMERS OR POLYMERS THEREOF

CROSS-REFERENCE TO RELATED APPLICATIONS

This is a national phase filing of International Application No. PCT/EP2003/007360, which was filed on Jul. 9, 2003 and published in English on Jan. 22, 2004, and is entitled to priority of European Patent Application No. 02254861.4 filed Jul. 10, 2002 and European Patent Application No. 02255549.4 filed Aug. 8, 2002.

FIELD OF THE INVENTION

The invention relates to an improved method for the preparation of polyorganosilylated carboxylate monomers or polymers. The invention further relates to said obtained polyorganosilylated carboxylate monomers or polymers and in another aspect, the invention relates to their use for the synthesis of hydrolysable polymers, such as binders for modern antifouling coatings.

BACKGROUND OF THE INVENTION

Antifouling paints are used in general to prevent and delay the fouling of underwater structures (e.g. ships' bottom, docks, fishnets, and buoys) caused by various marine organisms such as shells, seaweed and aquatic bacteria. When such aquatic organisms adhere and propagate on an underwater structure like the bottom of a ship, the surface roughness of the whole ship may be increased to induce decrease of velocity of the ship and subsequently increase of fuel consumption. The removal of these aquatic organisms from the ship's bottom requires much labour and a long period of working time. In addition, if these aquatic organisms adhere and propagate on an underwater structure such as a steel structure they deteriorate their anticorrosive coating films leading to a reduction of the lifetime of the underwater structure.

Underwater structures are therefore preferably coated with an antifouling paint employing polymers containing various hydrolysable groups and more specifically organosilyl groups. Several antifouling paints are known.

EP 0 297 505 for example relates to an antifouling paint that contains a polymer having organosilyl groups and/or organopolysiloxane groups in side chains. Since the organopolysiloxane group is derived from dehydrating condensation or like means of silicon oil with methacrylic acid, this document refers to a mixture of oligomers having different numbers of the recurrence of the organosiloxane group.

WO 84/02915 and JP 63215780 describe an antifouling paint of the hydrolysable self-polishing type employing a methacrylic ester polymer having triorganosilyl group in side chains or a similar polymer. Other examples related to the use of organosilyl acrylate polymers in antifouling compositions are EP 1 127 902, EP 1 127 925, JP 63118381, WO 96/38508, EP 0 802 243, EP 0 714 957, JP 07018216, JP 01132668, JP 01146969 and U.S. Pat. No. 4,957,989 hereby incorporated by reference.

The polymers used in the above-described antifouling paints are based on silylated carboxylate monomers.

Several processes are known as conventional techniques for the synthesis of said silylated carboxylate monomers.

JP 5306290 for example describes a process to obtain a methacrylic functional group-containing organosilicon compound. The process comprises reacting methacrylic acid with a halogenoalkylsilane e.g. trialkylsilylchloride in the presence of a tertiary amine compound having a cyclic structure. This process has disadvantages such as the reduced availability and storage stability of the silyl chloride. Moreover, the reaction yields as a by-product a hydrogen halide, which provokes the corrosion of the production equipment, or a halide salt, which has to be removed by filtration.

The synthesis of trimethylsilyl methacrylate from methacrylic acid and trimethylsilyl chloride is disclosed in Fedotov. et. al. Zh.Prikl.Khim. (1971), 44(3), 695. The synthesis of trimethylsilyl methacrylate from methacrylic acid and hexamethyldisilazane is described in A. Chapman & A. D. Jenkins J. Polym. Sci. Polym. Chem. Edn. vol 15, p. 3075 (1977). This method has the disadvantage of producing ammonia.

JP 10195084 discloses the reaction of unsaturated carboxylic acid such as acrylic acid or methacrylic acid with a trialkylsilylhydride compound in the presence of a copper catalyst. One of the disadvantages of this method is the risk of hydrogenation of the unsaturated carboxylic acid due to a side reaction of the produced H2 on the is carbon-carbon double bond.

U.S. Pat. No. 6,063,887 describes 1-acyloxyorganotetrasiloxane obtained by the reaction of hexamethylcylcotrisoloxane with an acyloxysilane.

An object of the present invention is to provide a novel process capable of readily preparing polyorganosilylated carboxylate monomers or polymers thereof in a high yield from easily available starting materials.

Another object of the present invention is to provide a more direct method for the synthesis of such polyorganosilylated carboxylate monomers or polymers thereof, with easy work-up procedures.

A further object of the present invention is to provide a novel process offering an improvement vis-à-vis of the disadvantages disclosed above.

SUMMARY OF THE INVENTION

The present invention relates to a process for the preparation of polyorganosilylated carboxylate monomers of general formula (I) or polymers thereof, comprising the steps of reacting a cyclosiloxane of formula $(R^4R^5SiO)_n$ with an unsaturated organosilylated carboxylate of formula (II) or a copolymer or a polymer thereof under the presence of a suitable catalyst, wherein $R^1$, $R^2$, $R^3$, $R^4$, $R^5$ each independently represent hydrogen, alkyl, alkenyl, alkynyl, alkyloxy, aryl, aralkyl or halogen radical optionally substituted by one or more substituents independently selected from the group comprising alkyl, aralkyl, aryl, hydroxy, halogen, amino or amino alkyl radicals, $R^6$ represents hydrogen, alkyl radical or —$CH_2$—$CO_2$—$SiR^1R^2R^3$, $R^7$ represents hydrogen, alkyl radical or —$COOR^9$ wherein $R^9$ represents an alkyl group, $R^8$ represents hydrogen, alkyl radical or —$CH_2$—$CO_2$—$(SiR^4R^5O)_n$—$SiR^1R^2R^3$, and n represents a number of dihydrocarbylsiloxane units from 3 to 20.

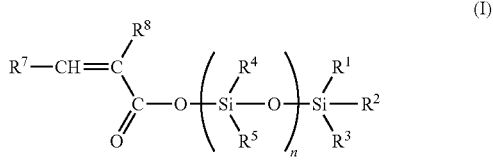

(I)

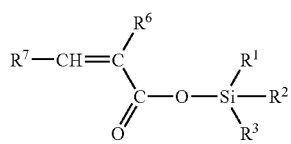

(II)

According to an embodiment of the present invention, $R^1$, $R^2$, $R^3$, $R^4$, $R^5$, $R^6$ and $R^9$ are each independently selected from the group comprising methyl, ethyl, propyl, isopropyl, isobutyl, n-butyl, sec-butyl, t-butyl. Preferably $R^1$, $R^2$, $R^3$, $R^4$, $R^5$, $R^6$ and $R^9$ are methyl.

According to another embodiment of the present invention, n represents a number of dihydrocarbylsiloxane units from 3 to 12, preferably from 3 to 8, more preferably from 3 to 6. In a preferred embodiment n is 3.

It was surprisingly found that by reacting cyclosiloxane with unsaturated organosilylated carboxylate monomers, polymers or copolymers thereof, polyorganosilylated carboxylates could be synthesized, when unsaturated organosilylated carboxylates are known to be not very reactive compounds and to polymerise easily.

DETAILED DESCRIPTION OF THE INVENTION

The present invention relates to a new process for the synthesis of polyorganosilylated carboxylate monomers of general formula (I) or polymers thereof, wherein a cyclosiloxane of formula $(R^4R^5SiO)_n$ is reacted with an unsaturated organosilylated carboxylate of formula (II) or copolymers or polymers thereof under the presence of a suitable catalyst, wherein $R^1$, $R^2$, $R^3$, $R^4$, $R^5$, $R^6$, $R^7$, $R^8$ and $R^9$ have the same meaning as that defined above.

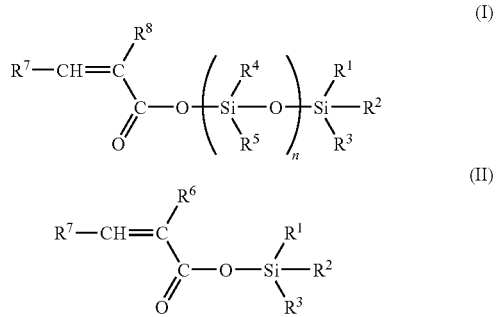

The process of the invention has the advantage of producing polyorganosilylated carboxylate monomers or polymers with exactly the desired number of the dihydrocarbylsilyloxane units.

The process according to the invention is characterized by a specific telomerisation. It was surprisingly found that the telomerisation of cyclosiloxane could be performed with unsaturated organosilylated carboxylate, which are not very reactive compounds and are known to polymerise easily.

The term 'telomerisation' as used herein refers to a process yielding low molecular weight monomers consisting of a chain of a limited number of units terminated at each end by a radical of a different compound (the telogen). See Oxford English Dictionary, Second Ed., Clarendon, Oxford, 1989. The telomerisation reaction proceeds as a polymerisation reaction between two substances providing respectively the terminal groups and internal linkages of the resulting telomer molecule. As used herein, the term "polymer" refers to the product of a polymerisation reaction, and is inclusive of homopolymers, copolymers, terpolymers, etc.

As used herein, the term "copolymer" refers to polymers formed by the polymerisation reaction of at least two different monomers.

As used herein, the term "independently selected" indicates that the each radical R so described, can be identical or different. For example each $R^4$ in compound of formula (I) may be different for each value of n.

The term "alkyl", as used herein, relates to saturated hydrocarbon radicals having straight, branched or cyclic moieties or combinations thereof and contains 1 to 20 carbon atoms, preferably 1 to 10 carbon atoms, more preferably 1 to 8 carbon atoms, still more preferably 1 to 6 carbon atoms, yet more preferably 1 to 4 carbon atoms. Examples of such radicals include methyl, ethyl, n-propyl, isopropyl n-butyl, isobutyl, set-butyl, tert-butyl, 2-methylbutyl, pentyl, iso-amyl, hexyl, cyclohexyl, 3-methylpentyl, octyl and the like.

The term "alkenyl", as used herein, relates to hydrocarbon radicals having one or several double bonds, having straight, branched or cyclic moieties or combinations thereof and containing from 2 to 18 carbon atoms, preferably 2 to 10 carbon atoms, more preferably from 2 to 8 carbon atoms, still more preferably 2 to 6 carbon atoms, yet more preferably 2 to 4 carbon atoms. Examples of alkenyl groups include vinyl, allyl, isopropenyl, pentenyl, hexenyl, heptenyl, cyclopropenyl, cyclobutenyl, cyclopentenyl, cyclohexenyl, 1-propenyl, 2-butenyl, 2-methyl-2-butenyl, isoprenyl, farnesyl, geranyl, geranylgeranyl and the like.

The term "alkynyl", as used herein, relates to hydrocarbon radicals having one or several triple bonds, having straight, branched or cyclic moieties or combinations thereof and having from 2 to 18 carbon atoms, preferably 2 to 10 carbon atoms, more preferably from 2 to 8 carbon atoms, still more preferably from 2 to 6 carbon atoms, yet more preferably 2 to 4 carbon atoms. Examples of alkynyl radicals include ethynyl, propynyl, (propargyl), butynyl, pentynyl, hexynyl and the like.

The term "aryl" as used herein, relates to an organic radical derived from an aromatic hydrocarbon by removal of one hydrogen, and includes any monocyclic or bicyclic carbon ring of up to 7 members in each ring, wherein at least one ring is aromatic. Said radical may be optionally substituted with one or more substituents independently selected from alkyl, alkoxy, halogen, hydroxy or amino radicals. Examples of aryl includes phenyl, p-tolyl, 4-methoxyphenyl, 4-(tert-butoxy)phenyl, 3-methyl-4-methoxyphenyl, 4-fluorophenyl, 4-chlorophenyl, 3-nitrophenyl, 3-aminophenyl, 3-acetamidophenyl, 4-acetamidophenyl, 2-methyl-3-acetamidophenyl, 2-methyl-3-aminophenyl, 3-methyl-4-aminophenyl, 2-amino-3-methylphenyl, 2,4-dimethyl-3-aminophenyl, 4-hydroxyphenyl, 3-methyl-4-hydroxyphenyl, 1-naphthyl, 2-naphthyl, 3-amino-1-naphthyl, 2-methyl-3-amino-1-naphthyl, 6-amino-2-naphthyl, 4,6-dimethoxy-2-naphthyl, tetrahydronaphthyl, indanyl, biphenyl, phenanthryl, anthryl or acenaphthyl and the like.

The term "aralkyl" as used herein, relates to a group of the formula alkyl-aryl, in which alkyl and aryl have the same meaning as defined above. Examples of aralkyl radicals include benzyl, phenethyl, dibenzylmethyl, methylphenylmethyl, 3-(2-naphthyl)-butyl, and the like.

The process according to the invention consists of subjecting a cyclosiloxane of formula $(R^4R^5SiO)_n$ to a ring-opening reaction with an unsaturated organosilylated carboxylate of formula (II) or a copolymer or a polymer thereof, in the presence of a suitable catalyst and with or without solvent. The reaction is preferably set up in such a way that each mole of cyclosiloxane is treated with at least one mole of unsaturated organosilylated carboxylate of formula (II) or with a copolymer or a polymer of said carboxylate.

The reaction can be performed with or without solvents. Suitable solvents which can be used in the process according to the invention are nonpolar inert solvents such as for example benzene, toluene, xylene, mesitylene or ethylbenzene, aliphatic hydrocarbons, typically pentane, hexane, cyclohexane, heptane, octane, decane or decahydronaphthalene, noncyclic ethers, typically diethyl ether, diisopropyl ether, diisopropyl ether or diisobutyl ether, or mixtures thereof. In a preferred embodiment, said solvent is toluene.

Examples of the cyclosiloxanes which may be employed in the present process are described in the "Encyclopedia of Polymer Science and Engineering", Mark et al., eds., 2nd ed., John Wiley & Sons (1989), Vol. 15, p. 207 et seq., the contents of which are incorporated by reference herein. Examples of suitable cyclosiloxanes of formula $(R^4R^5SiO)_n$ for use in the process according to the invention include but is not limited to 1,1,3,3,5,5-hexamethyl-cyclotrisiloxane (D3), 1,1,3,3,5,5-hexaethyl-cyclotrisiloxane, 1,1,3,3,5,5-hexaphenyl-cyclotrisiloxane, 1,1,3,3,5,5-hexavinyl-cyclotrisiloxane, 1,3,5-trimethyl-1,3,5-trivinyl-cyclotrisiloxane, 1,3,5-trimethyl-1,3,5-triphenyl-cyclotrisiloxane, 1,3,5-trimethyl-1,3,5-tripropyl-cyclotrisiloxane, 1,3,5-triethyl-1,3,5-trimethyl-cyclotrisiloxane, 1,3,5-trimethyl-1,3,5-triphenethyl-cyclosiloxane, 1,3,5-trivinyltrihydro-cyclotrisiloxane, 1,3,5-trimethyltrihydro-cyclotrisiloxane, pentamethyl-cyclotrisiloxanes, 1,3,5-trimethyl-1,3,5-tris(3',3',3'-trifluoropropyl)-cyclotrisiloxane (F3), 1,1,3,3,5,5,7,7-octamethyl-cyclotetrasiloxane (D4), 1,1,3,3,5,5,7,7-octaphenyl-cyclotetrasiloxane, 1,1,3,3,5,5,7,7-octavinyl-cyclotetrasiloxane, 1,3,5,7-tetramethyl-1,3,5,7-tetrahydro-cyclotetrasiloxane, 1,3,5,7-tetramethyl-1,3,5,7-tetra(1-octyl)-cyclotetrasiloxane, 1,3,5,7-tetravinyl-1,3,5,7-tetramethyl-cyclotetrasiloxane, 1,3,5,7-tetravinyl-1,3,5,7-tetraethyl-cyclotetrasiloxane, 1,3,5,7-tetraallyl-1,3,5,7-tetraphenyl-cyclotetrasiloxane, 1,3,5,7-tetra(1-hexadecyl)-1,3,5,7-tetramethyl-cyclotetrasiloxane, 1,3,5,7-tetraoctyltetrahydro-cyclotetrasiloxane, 1,3,5,7-tetravinyltetrahydro-cyclotetrasiloxane, 1,3,5,7-tetraethyltetrahydro-cyclotetrasiloxane, 1,3,5,7-tetrapropenyltetrahydro-cyclotetrasiloxane, 1,3,5,7-tetrapentenyltetrapentyl-cyclotetrasiloxane, 1,3,5,7-tetraphenyltetrahydro-cyclotetrasiloxane, pentamethyl-cyclotetrasiloxanes, hexamethyl-cyclotetrasiloxanes, 1,3,5,7-tetramethyl-1,3,5,7-tetrakis (3',3',3'-trifluoropropyl)-cyclotetrasiloxane (F4) 1,1,3,3,5,5,7,7,9,9-decamethyl-cyclopentasiloxane (D5), 1,3,5,7,9-pentavinyl-1,3,5,7,9-pentamethyl-cyclopentasiloxane, 1,3,5,7,9-pentadecenyl-1,3,5,7,9-pentapropyl-cyclopentasiloxane, 1,3,5,7,9-pentamethylpentahydro-cyclopentasiloxane, 1,3,5,7,9-pentavinylpentahydro-cyclopentasiloxane, tetramethyl-cyclopentasiloxanes, hexamethyl-cyclopentasiloxanes, heptamethyl-cyclopentasiloxanes, 1,1,3,3,5,5,7,7,9,9,11,11-dodecamethyl-cyclohexasiloxane (D6), 1,3,5,7,9,11-hexavinylhexamethyl-cyclohexasiloxane, 1,3,5,7,9,11-hexamethylhexahydro-cyclohexasiloxane, tetramethyl-cyclohexasiloxanes, pentamethyl-cyclohexasiloxanes, 1,3,5,7,9,11,13,15,17,19-decavinyldecahydro-cyclodecasiloxane, 1,3,5,7,9,11,13,15,17,19,21,23,25,27,29-pentadecavinylpentadecahydro-cyclopentadecasiloxane and the like.

In a preferred embodiment, said cyclosiloxane of formula $(R^4R^5SiO)_n$ is selected from the group comprising 1,1,3,3,5,5-hexamethyl-cyclotrisiloxane (D3), 1,1,3,3,5,5,7,7-octamethyl-cyclotetrasiloxane (D4), 1,1,3,3,5,5,7,7,9,9-decamethyl-cyclopentasiloxane (D5), 1,1,3,3,5,5,7,7,9,9,11,11-dodecamethyl-cyclohexasiloxane (D6). More preferably said cyclosiloxane of formula $(R^4R^5SiO)_n$ is 1,1,3,3,5,5-hexamethyl-cyclotrisiloxane (D3). Examples of the unsaturated organosilylated carboxylate of formula (II) which can be used in the process according to the invention include but are not limited to trimethylsilyl (meth)acrylate, tri-t-butylsilyl (meth)acrylate, tribenzylsilyl (meth)acrylate, triethylsilyl (meth)acrylate, tri-isopropylsilyl (meth)acrylate, triisobutylsilyl (meth)acrylate, tri-n-amylsilyl (meth)acrylate, tri-n-butylsilyl (meth)acrylate, tri-n-dodecylsilyl (meth)acrylate, tri-n-hexylsilyl (meth)acrylate, tri-n-octylsilyl (meth)acrylate, tri-n-propylsilyl (meth)acrylate, triphenylsilyl (meth)acrylate, tri-p-methylphenylsilyl (meth)acrylate, dibutylcyclohexylsilyl (meth)acrylate, dibutylphenylsilyl (meth)acrylate; dicyclohexylphenylsilyl (meth)acrylate, diisopropyl-n-butylsilyl (meth)acrylate, diisopropylstearylsilyl (meth)acrylate, dimethylbutylsilyl (meth)acrylate, dimethylcyclohexylsilyl (meth)acrylate, dimethylhexylsilyl (meth)acrylate, dimethyloctylsilyl (meth)acrylate, dimethylphenylsilyl (meth)acrylate, ethyldibutylsilyl (meth)acrylate, ethyldimethylsilyl (meth)acrylate, lauryldiphenylsilyl (meth)acrylate, methyldibutylsilyl (meth)acrylate, n-octyldi-n-butylsilyl (meth)acrylate, t-butyl dimethylsilyl (meth)acrylate t-butyldiphenylsilyl (meth)acrylate, bis (trimethylsilyl) itaconate, t-butyldiphenylsilyl methyl fumarate, t-butyldiphenylsilyl methyl maleate, t-butyldiphenylsilyl n-butyl fumarate, t-butyldiphenylsilyl n-butyl maleate, triisopropylsilyl amyl fumarate, triisopropylsilyl amyl maleate, triisopropylsilyl methyl fumarate, triisopropylsilyl methyl maleate, tri-n-butylsilyl n-butyl fumarate, tri-n-butylsilyl n-butyl maleate, and the like and polymers or copolymers thereof, wherein methacrylate or acrylate is herein collectively referred to as a "(meth)acrylate".

In a preferred embodiment, said organosilylated carboxylate of formula (II) is selected from the group comprising trimethylsilyl (meth)acrylate, tri t-butylsilyl (meth)acrylate, tribenzylsilyl (meth)acrylate, triethylsilyl (meth)acrylate, tri-isopropylsilyl (meth)acrylate, triisobutylsilyl (meth)acrylate, tri-n-amylsilyl (meth)acrylate, tri-n-butylsilyl (meth)acrylate, tri-n-dodecylsilyl (meth)acrylate, tri-n-hexylsilyl (meth) acrylate, tri-n-octylsilyl (meth)acrylate, tri-n-propylsilyl (meth)acrylate and triphenylsilyl (meth)acrylate and copolymers or polymers thereof. More preferably said organosilylated carboxylate of formula (II) is trimethylsilyl methacrylate or a copolymer or a polymer thereof.

This process can be suitably applied to unsaturated organosilylated carboxylate copolymers or polymers. The reaction is performed in such a way that the trialkylsilyl carboxylate functions present in the copolymer or polymer are selectively converted into polyorganosilyl function.

Suitable unsaturated organosilylated carboxylate copolymers or polymers can be obtained using processes known in the art by polymerisation of unsaturated organosilylated carboxylate monomers of formula (II), and/or by polymerisation with various other monomers such as vinyl monomers including acrylic esters, methacrylic esters, styrene, vinyl esters (e.g., vinyl acetate, vinyl propionate, vinyl butyrate, vinyl benzoate), vinyltoluene, alpha-methylstyrene, crotonic esters, and itaconic esters.

The polymers or copolymers of the unsaturated organosilylated carboxylate of formula (II) can be prepared by addition polymerisation of the appropriate monomers in the appropriate proportions at polymerisation conditions using a free radical catalyst such as e.g. benzoyl peroxide, tert-butyl peroxy 2-ethyl hexanoate (TBPEH), t-butyl peroxybenzoate (TBP), or azobisisobutyronitrile. The reaction is carried out in an organic solvent such as e.g. xylene, toluene, amides such as N-methylpyrrolidone and N,N-dimethylformamide, ethers such as dioxane, THF and diethyl ether, butyl acetate, n-butanol, 2-ethoxyethanol, cyclohexanone, methyl-isoamyl ketone, 2-methoxyethanol, 2-butoxyethanol, 2-ethoxyethyl acetate, and mixtures thereof. Polymerisation is preferably carried out at a temperature in the range of 70-140° C. although higher temperatures may be used providing that the solvent and the catalyst are adapted thereto. Within this range the use of higher temperatures produces polymers of lower molecular weight. Polymerisation maybe carried out by heating all the polymer ingredients in the solvent or preferably by gradually adding the monomers and catalyst to the heated solvent. The latter procedure produces polymers of lower molecular weight.

Examples of suitable catalyst for the reaction include but are not limited to acidic catalyst. Examples of acid catalysts include proton acid catalysts and Lewis acid catalysts. In a preferred embodiment, the proton acid catalysts suitable for use in the present process include but are not limited to hydrochloric acid, nitric acid, acetic acid, sulfuric acid, trifluoromethanesulfonic acid, trifluoroacetic acid. In a preferred embodiment, trifluoromethanesulfonic acid is used. Said acid catalyst may be a heterogeneous acids such as the strongly acidic ion exchange resins, all of which are of the sulfonic type. Examples of commercially available strongly acidic ion exchange resins of the sulfonic type are those known by the trade names AMBERLYST A15, AMBERLYST 38 W, AMBERLYST 36, AMBERJET 1500H, AMBERJET 1200H, (AMBERJET is a trademark of Rohm and Haas Company) DOWEX MSC-1, DOWEX 50W (DOWEX is a trademark of Dow Chemical Company), DELOXAN ASP I/9 (DELOXAN is a trademark of Degussa), DIAION SK1B (DIAION is a trademark of Mitsubishi), LEWATIT VP OC 1812, LEWATIT S 100 MB, LEWATIT S 100 G1 (LEWATIT is a trademark of Bayer), NAFION SAC13, NAFION NR50 (NAFION is a trademark of DuPont) and CT275 (a macroporous resin with a medium pore diameter in the range of from 600 to 750, available from Purlite). In another embodiment, suitable Lewis acid catalysts include but are not limited to $ZnCl_2$, $BeCl_2$, $TiCl_4$, $SnCl_4$, $FeCl_3$, $FeCl_2$, $SbCl_5$, $AlCl_3$ and other metal halides. Co-catalysts such as acetic acid may also be used in the process according to the invention.

Because they permit the suppression of equilibration reactions due to siloxane bond rearrangement, selectively bringing about the ring-opening reaction of the cyclosiloxane, and can suppress undesirable side reactions, metal halides exhibiting Lewis acid properties are particularly useful. In a preferred embodiment, the catalyst used during the reaction is $ZnCl_2$. When a heterogeneous acid is used in the process according to the invention, this has the advantage of easier separation from the reaction product. In a preferred embodiment, AMBERLYST A15 is used. When the reaction is performed with copolymers of unsaturated organosilylated carboxylate, the use of heterogeneous catalysts is preferred because it offers the advantage of being easily removed from the resin at the end of the process.

The telomerisation reaction between the cyclosiloxane and the unsaturated organosilylated carboxylate can be preformed at a temperature selected in the range of 20 to 150° C., preferably 50 to 120° C., more preferably 90 to 110° C. In another preferred embodiment said reaction is performed at room temperature.

The reaction may be conducted with or without added polymerisation inhibitor. The polymerisation inhibitors which can be used in the process of the invention are preferably phenolic stabilizers such as cresol or hydroquinone derivatives, e.g. bis(tert-butyl)cresol, 2,5-di-tert-butylhydroquinone, 4-methoxy-phenol, 2,6-di-tert-butyl-4-methylphenol or the monomethyl ether of hydroquinone or phenothiazine, in a concentration ranging from 0.001% to 2% by weight, preferably from 0.002% to 0.7% by weight, based on the total weight of cyclosiloxane and unsaturated organosilylated carboxylate (II).

The ring-opening reaction may be terminated by neutralizing the acidic catalyst with a suitable base which may be selected from the group comprising triethylamine, diethylamine, tributylamine, hexamethyldisilazane N-methylmorpholine, diisopropylethylamine, dicyclohexylamine, N-methylpiperidine, pyridine, 4-pyrrolidinopyridine, picoline, 4-(N,N-dimethylamino)pyridine, 2,6-di(t-butyl)-4-methylpyridine, quinoline, N,N-dimethylaniline, N,N-diethylaniline and the like. In a preferred embodiment said base is triethylamine. The salts produced during this neutralization reaction can be removed by filtration or decantation.

The polyorganosilylated carboxylate compound of formula (I) can be isolated by distillation under reduced pressure. The reaction progress may be monitored by any suitable analytical method. The polymer of polyorganosilylated carboxylate compound of formula (I) can be isolated by filtrating the catalyst at the end of the reaction.

The present invention further relates to polyorganosilylated carboxylate monomers of formula (I) or polymers thereof, which may be obtainable by the process according to the invention. In another embodiment the present invention relates to polyorganosilylated carboxylate monomers or polymers obtained by the process according to the invention. In a preferred embodiment, $R^1$, $R^2$, $R^3$, $R^4$, $R^5$, $R^6$ and $R^9$ in compound of formula (I) are each independently selected from the group comprising methyl, ethyl, propyl, isopropyl, isobutyl, n-butyl, sec-butyl, t-butyl. More preferably $R^1$, $R^2$, $R^3$, $R^4$, $R^5$, $R^6$ and $R^9$ are methyl. In another preferred embodiment, n is selected such as to represents a number of dihydrocarbylsiloxane units from 3 to 12, preferably from 3 to 8, more preferably from 3 to 6. In a more preferred embodiment, n is 3.

Examples of the polyorganosilylated carboxylate monomers obtained by the process of the invention include but are not limited to nonamethyl-1-(meth)acryloyloxy-tetrasiloxane, nonaethyl-1-(meth)acryloyloxy-tetrasiloxane, nona-t-butyl-1-(meth)acryloyloxy-tetrasiloxane, nonabenzyl-1-(meth)acryloyloxy-tetrasiloxane, nona-isopropyl-1-(meth)acryloyloxy-tetrasiloxane, nona-n-propyl-1-(meth)acryloyloxy-tetrasiloxane, nona-isobutyl-1-(meth)acryloyloxy-tetrasiloxane, nona-amyl-1-(meth)acryloyloxy-tetrasiloxane, nona-n-butyl-1-(meth)acryloyloxy-tetrasiloxane, nona-dodecyl-1-(meth)acryloyloxy-tetrasiloxane, nona-hexyl-1-(meth)acryloyloxy-tetrasiloxane, nona-phenyl-1-(meth)acryloyloxy-tetrasiloxane, nona-octyl-1-(meth)acryloyloxy-tetrasiloxane, undecamethyl-1-(meth)acryloyloxy-pentasiloxane, undecaethyl-1-(meth)acryloyloxy-pentasiloxane, undeca-t-butyl-1-(meth)acryloyloxy-pentasiloxane, undecabenzyl-1-(meth)acryloyloxy-pentasiloxane, undeca-isopropyl-1-(meth)acryloyloxy-pentasiloxane, undeca-n-propyl-1-(meth)acryloyloxy-pentasiloxane, undeca-isobutyl-1-(meth)acryloyloxy-pentasiloxane, undeca-amyl-1-(meth)acryloyloxy-pentasiloxane, undeca-n-butyl-1-(meth)acryloyloxy-pentasiloxane, undeca-dodecyl-1-(meth)acryloyloxy-pentasiloxane, undeca-hexyl-1-(meth)acryloyloxy-pentasiloxane, undeca-phenyl-1-(meth)acryloyloxy-pentasiloxane, undeca-octyl-1-(meth)acryloyloxy-pentasiloxane tridecamethyl-1-(meth)acryloyloxy-hexasiloxane, tridecaethyl-1-(meth)acryloyloxy-hexasiloxane, trideca-t-butyl-1-(meth)acryloyloxy-hexasiloxane, tridecabenzyl-1-(meth)acryloyloxy-hexasiloxane, trideca-isopropyl-1-(meth)acryloyloxy-hexasiloxane, trideca-n-propyl-1-(meth)acryloyloxy-hexasiloxane, trideca-isobutyl-1-(meth)acryloyloxy-hexasiloxane, trideca-amyl-1-(meth)acryloyloxy-hexasiloxane, trideca-n-butyl-1-(meth)acryloyloxy-hexasiloxane, trideca-dodecyl-1-(meth)acryloyloxy-hexasiloxane, trideca-hexyl-1-(meth)acryloyloxy-hexasiloxane, trideca-phenyl-1-(meth)acryloyloxy-hexasiloxane, trideca-octyl-1-(meth)acryloyloxy-hexasiloxane and polymers thereof The advantage of this invention is that the process uses reactants, which can be easily handled. Another advantage lies in the simplicity and safety of the procedure (no trapping of corrosive gaseous matter). Furthermore, another advantage is that the reaction is a one step procedure. Also no degradation of the material occurs. Due to its shortness, its easy work-up procedure and its high yield the process of the present invention can be considered as a substantial improvement over the existing methods described above.

Still another advantage of the invention is that the polyorganosilylated carboxylate monomers or polymers obtained by the process according to the invention have the exactly desired number of dihydrocarbylsilyloxy units. The polyorganosilylated carboxylate monomers obtained by the process of the invention can be polymerised with various other monomers such as vinyl monomers including acrylic esters, methacrylic esters, styrene, vinyl esters (e.g., vinyl acetate, vinyl propionate, vinyl butyrate, vinyl benzoate), vinyltoluene, alpha-methylstyrene, crotonic esters, and itaconic esters.

The polymers and copolymers of said monomers are useful in coating or paint composition. More preferably they are used as comonomer unit in the binder of antifouling coating compositions. When used in an antifouling coating composition, they give a film which undergoes neither cracking nor peeling and shows moderate hydrolysability to dissolve into seawater constantly at an adequate rate and which therefore exhibits excellent antifouling property for long term.

The antifouling coating compositions prepared using the monomers obtained by the process of the invention are tin-free coatings and provide an alternative to the present self-polishing coating technology based on hydrolysable tributyl-tin polymers (the use of which is due to be banned in antifouling paints by 2003). The polyorganosilylated carboxylate monomers provided by the process of the invention compared to organotin compounds are less toxic, less polar, more hydrophobic and more stable.

The invention will be more readily understood by reference to the following examples, which are included merely for purposes of illustration of certain aspects and embodiments of the present invention and are not intended to limit the invention.

EXAMPLES

In the following examples, NMR data have been determined in $CDCl_3$ and are expressed as delta versus TMS. Unless otherwise stated, all the reactants were purchased from Aldrich and were used without purification.

Example 1

50 g of hexamethylcyclotrisiloxane, 35.6 g of trimethylsilyl methacrylate, 2.5 g of zinc chloride and 0.4 g of 4-methoxy phenol were dissolved in 50 ml of toluene. After 11 h at 100° C., the mixture was allowed to cool until room temperature, 40 ml of triethylamine were then added and the salts were filtered. After evaporation of the solvent, distillation under reduced pressure (0.3 mbar, 80° C.) furnished pure nonamethyl-1-methacryloyloxy-tetrasiloxane.

$^{13}C$ NMR: 167.0, 137.7, 126.4, 18.5, 2.0, 1.3, 1.1, 0.0;
$^{29}Si$ NMR: 7.3, −8.6, −20.1, −21.0;
IR (film): 2963, 1707, 1638, 1335, 1310, 1261, 1179, 1082, 1044, 842, 804 $cm^{-1}$.

Example 2

5 g of hexamethylcyclotrisiloxane, 3.5 g of trimethylsilyl methacrylate, 0.016 g of trifluoromethane sulfonic acid were stirred for 24 h at room temperature. 0.5 ml of triethylamine was then added, and the salts were filtered to furnish nonamethyl-1-methacryloyloxy-tetrasiloxane.

Example 3

5 g of hexamethylcyclotrisiloxane, 3.5 g of trimethylsilyl methacrylate and 0.3 g of Amberlyst A15 resin catalyst were stirred in 2.5 ml of toluene. After 7 h at room temperature the catalyst was filtered and the solvent evaporated under reduced pressure to furnish nonamethyl-1-methacryloyloxy-tetrasiloxane.

The use of AMBERLYST A15 resin catalyst, which is an insoluble acidic resin, provides the advantages of allowing a clean transformation at room temperature. Furthermore it is easily removed by filtration.

Example 4

5 g of hexamethylcyclotrisiloxane, 4.4 g of triethylsilyl methacrylate and 0.3 g of Amberlyst A15 resin were stirred in 2.5 ml of toluene. After 7 h at room temperature, the catalyst was filtered and the solvent evaporated under reduced pressure to furnish 1,1,1-triethyl-2,2,3,3,4,4-hexamethyl-1-methacryloyloxy-tetrasiloxane.

The compound was characterised by GC-MS. Column: HP5 (30 m/i.d.:0.32 mm i.d./thickness:0.25 microns), initial temperature: 70° C., final temperature: 300° C., rate: 10° C./min, retention time: 11.2 min. EIMS: $M^+$.: 422 (<1%), 407 (100%), 393 (85%)., 309 (5%), 253 (10%), 217 (10%);

IR (film): 2961, 2881, 1704, 1637, 1336, 1261, 1178, 1088, 1023, 808 $cm^{-1}$.

Example 5

100 g of xylene was added to a 2 l 4-necks flask and kept under nitrogen. The four necks of the flask were equipped with stirrings means, a reflux condenser, a thermometer for temperature control of the reaction, and means for addition of the monomers.

A premix was prepared in a separate vessel, containing:
148.5 g of methyl methacrylate
346.5 g of butyl acrylate
49.5 g of trimethylsilyl methacrylate
9.9 g (=2% on total monomer weight) t-Butyl peroxy-2-ethyl hexanoate (=TBPEH sold under the name Trigonox 21S by Akzo-Nobel)

The premix was added drop by drop to the reaction vessel (total time=3 hours) whilst maintaining the temperature at 90° C. Thirty minutes after the end of the addition of the premix, five post-additions of 0.1% TBPEH were made at intervals of 45 minutes. 15 minutes after the last post addition, the temperature was increased up to 120° C. during one hour. After cooling the binder solution was thinned with 98 g of xylene to a viscosity of 14 dPa·s.

66.5 g of hexamethylcyclotrisiloxane and 1 g of Amberlyst A15 resin were added to the binder. After 5 h at room temperature, the catalyst was filtered and the binder was diluted with xylene to a viscosity of 14 dPa·s.

The NMR spectra of the obtained polymer was found to be identical to the NMR spectra of the polymer obtained by polymerising nonamethyl-1-methacryloyloxy-tetrasiloxane. It was surprisingly found that the telomerisation of hexamethylcyclotrisiloxane could be performed with silyl methacrylates or polymers or copolymers thereof, which were known to be less reactive, and prone to polymerisation. A clean conversion was observed (GC) and no oligomerisation of the formed polysilyl methacrylate was observed. The product was easily purified by distillation. When the polymer was synthesised, it was isolated by simply eliminating the catalyst.

The process according to the invention has the advantage of being a one step process. Moreover during said process there is no release of corrosive matter. The purification of the product produced is straightforward and there is a good control of the MW of the polydimethyl siloxane produced. Furthermore the polydialkylsiloxane units do not undergo fragmentation or oligomerisation during the reaction.

While the invention has been described in detail and with reference to specific embodiments thereof, it will be apparent to one skilled in the art that various changes and modifications can be made therein without departing from the spirit and scope thereof.

The invention claimed is:

1. Process for the preparation of polyorganosilylated carboxylate monomers of general formula (I) comprising the steps of:

$$R^7-CH=C\begin{matrix}R^8\\ \\C-O\end{matrix}\left(\begin{matrix}R^4\\|\\Si-O\\|\\R^5\end{matrix}\right)_n\begin{matrix}R^1\\|\\Si-R^2\\|\\R^3\end{matrix}$$ (I)

reacting a cyclosiloxane of formula $(R^4R^5SiO)_n$ with unsaturated organosilylated carboxylate of formula (II) or copolymers thereof under the presence of a suitable catalyst, $$R^7-CH=C\begin{matrix}R^6\\ \\C-O-Si-R^2\\|\\O\end{matrix}\begin{matrix}R^1\\|\\R^3\end{matrix}$$ (II)

wherein $R^1$, $R^2$, $R^3$, $R^4$, $R^5$ each independently represent hydrogen, alkyl, alkenyl, alkynyl, alkyloxy, aryl, aralkyl or halogen radical optionally substituted by one or more substituents independently selected from the group comprising alkyl, aralkyl, aryl, hydroxy, halogen, amino or amino alkyl radicals, $R^6$ represents hydrogen, alkyl radical, or $-CH_2-CO_2-SiR^1R^2R^3$, $R^7$ represents hydrogen, alkyl radical or $-COOR^9$ wherein $R^9$ represents an alkyl group, $R^8$ represents hydrogen, alkyl radical or $-CH_2-CO_2-(SiR^4R^5O)_n-SiR^1R^2R^3$, and n represents a number of dihydrocarbylsiloxane units from 3 to 20.

2. Process according to claim 1, wherein $R^1$, $R^2$, $R^3$, $R^4$, $R^5$, $R^6$ and $R^9$ are each independently selected from the group comprising methyl, ethyl, propyl, isopropyl, isobutyl, n-butyl, sec-butyl, and t-butyl.

3. Process according to claim 2, wherein $R^1$, $R^2$, $R^3$, $R^4$, $R^5$, $R^6$ and $R^9$ are methyl.

4. Process according to claim 1, wherein n represents a number of dihydrocarbylsiloxane units from 3 to 12.

5. Process according to claim 4, wherein n is 3.

6. Process according to claim 1, wherein said unsaturated organosilylated carboxylate of formula (II) is selected from the group comprising trimethylsilyl (meth)acrylate, tri-t-butylsilyl (meth)acrylate, tribenzylsilyl (meth) acrylate, triethylsilyl (meth)acrylate, tri-isopropylsilyl (meth)acrylate, tri-isobutylsilyl (meth)acrylate, tri-n-amylsilyl (meth)acrylate, tri-n-butylsilyl (meth)acrylate, tri-n-octylsilyl (meth)acrylate, tri-n-hexylsilyl (meth)acrylate, tri-n-octylsilyl (meth) acrylate, tri-n-propylsilyl (meth)acrylate, triphenylsilyl (meth)acrylate, tri-p-methylphenylsilyl (meth)acrylate, dibutylcyclohexylsilyl (meth)acrylate, dibutylphenylsilyl (meth) acrylate; dicyclohexylphenylsilyl (meth)acrylate, diisopropyl-n-butylsilyl (meth)acrylate, diisopropylstearylsilyl (meth)acrylate, dimethylbutylsilyl (meth)acrylate, dimethylcyclohexylsilyl (meth)acrylate, dimethylhexylsilyl (meth) acrylate, dimethyloctylsilyl (meth)acrylate, dimethylphenylsilyl (meth)acrylate, ethyldibutylsilyl (meth)acrylate, ethyldimethylsilyl (meth)acrylate, lauryldiphenylsilyl (meth) acrylate, methyldibutylsilyl (meth)acrylate, n-octyldi-n-butylsilyl (meth)acrylate, t-butyl dimethylsilyl (meth) acrylate, t-butyldiphenylsilyl (meth)acrylate, bis (trimethylsilyl) itaconate, t-butyldiphenylsilyl methyl fumarate, t-butyldiphenylsilyl methyl maleate, t-butyldiphenylsilyl n-butyl fumarate, t-butyldiphenylsilyl n-butyl maleate, triisopropylsilyl amyl fumarate, triisopropylsilyl amyl maleate, triisopropylsilyl methyl fumarate, triisopropylsilyl methyl maleate, tri-n-butylsilyl n-butyl fumarate, tri-n-butylsilyl n-butyl maleate, and polymers or copolymers thereof and the like.

7. Process according to claim 6, wherein said unsaturated organosilylated carboxylate of formula (II) is selected from the group comprising trimethylsilyl (meth) acrylate, tri-t-butylsilyl (meth)acrylate, tribenzylsilyl (meth)acrylate, triethylsilyl (meth) acrylate, tri-isopropylsilyl (meth)acrylate, tri-isobutylsilyl (meth)acrylate, tri-n-amylsilyl (meth)acrylate, tri-n-butylsilyl (meth)acrylate, tri-n-dodecylsilyl (meth) acrylate, tri-n-hexylsilyl (meth)acrylate, tri-n-octylsilyl (meth)acrylate, tri-n-propylsilyl (meth) acrylate and triphenylsilyl (meth)acrylate and polymers or copolymers thereof.

8. Process according to claim 7, wherein said unsaturated organosilylated carboxylate of formula (II) is trimethylsilyl methacrylate or a copolymer or a polymer thereof.

9. Process according to claim 1, wherein said cyclosiloxane of formula $(R^4R^5SiO)_n$ is selected from the group comprising 1,1,3,3,5,5-hexamethyl-cyclotrisiloxane, 1,1,3,3,5,5-hexaethyl-cyclotrisiloxane, 1,1,3,3,5,5-hexaphenyl-cyclotrisiloxane, 1,1,3,3,5,5-hexavinyl-cyclotrisiloxane, 1,3,5-trimethyl-1,3,5-trivinyl-cyclotrisiloxane, 1,3,5-trimethyl-1,3,5-triphenyl-cyclotrisiloxane, 1,3,5-trimethyl-1,3,5-tripropyl-cyclotrisiloxane, 1,3,5-triethyl-1,3,5-trimethyl-cyclotrisiloxane, 1,3,5-trimethyl-1,3,5-triphenethyl-cyclosiloxane, 1,3,5-trivinyltrihydro-cyclotrisiloxane, 1,3,5- trimethyltrihydro-cyclotrisiloxane, pentamethyl-cyclotrisiloxanes, 1,1,3,3,5,5,7,7-octamethyl-cyclotetrasiloxane, 1,1,3,3,5,5,7,7-octaphenyl-cyclotetrasiloxane, 1,1,3,3,5,5,7,7-octavinyl-cyclotetrasiloxane, 1,1,3,3,5,5,7,7-octahydro-cyclotetrasiloxane, 1,3,5,7-tetramethyl-1,3,5,7-tetrahydro-cyclotetrasiloxane, 1,3,5,7-tetramethyl-1,3,5,7-tetra(1-octyl)-cyclotetrasiloxane, 1,3,5,7-tetravinyl-1,3,5,7-tetramethyl-cyclotetrasiloxane, 1,3,5,7-tetravinyl-1,3,5,7-tetraethyl cyclotetrasiloxane, 1,3,5,7-tetraallyl-1,3,5,7-tetraphenyl-cyclotetrasiloxane, 1,3,5,7-tetra(1-hexadecyl)-1,3,5,7-tetramethyl-cyclotetrasiloxane, 1,3,5,7-tetraoctyltetrahydro-cyclotetrasiloxane, 1,3,5,7-tetravinyltetrahydro-cyclotetrasiloxane, 1,3,5,7-tetraethyltetrahydro-cyclotetrasiloxane, 1,3,5,7-tetrapropenyltetrahydro-cyclotetrasiloxane, 1,3,5,7-tetrapentenyltetrapentyl-cyclotetrasiloxane; 1,3,5,7-tetraphenyltetrahydro-cyclotetrasiloxane, pentamethyl-cyclotetrasiloxanes, hexamethyl-cyclotetrasiloxanes, 1,1,3,3,5,5,7,7,9,9-decamethyl-cyclopentasiloxane, 1,1,3,3,5,5,7,7,9,9-decahydro-cyclopentasiloxane, 1,3,5,7,9-pentavinyl-1,3,5,7,9-pentamethyl-cyclopentasiloxane, 1,3,5,7,9-pentadecenyl-1,3,5,7,9-pentapropyl-cyclopentasiloxane, 1,3,5,7,9-pentamethylpentahydro-cyclopentasiloxane, 1,3,5,7,9-pentavinylpentahydro-cyclopentasiloxane, tetramethyl-cyclopentasiloxanes, hexamethyl-cyclopentasiloxanes, heptamethyl-cyclopentasiloxanes, 1,1,3,3,5,5,7,7,9,9,11,11-dodecamethyl-cyclohexasiloxane, 1,1,3,3,5,5,7,7,9,9,11,11-dodecahydro-cyclohexasiloxane, 1,3,5,7,9,11-hexavinylhexamethyl-cyclohexasiloxane, 1,3,5,7,9,11-hexamethylhexahydro-cyclohexasiloxane, tetramethyl-cyclohexasiloxanes, pentamethyl-cyclohexasiloxanes, 1,3,5,7,9,11,13,15,17,19-decavinyldecahydro-cyclodecasiloxane, 1,3,5,7,9,11,13,15,17,19,21,23,25,27,29-pentadecavinyl-pentadecahydro-cyclopentadecasiloxane and the like.

10. Process according to claim 9, wherein said cyclosiloxane of formula $(R^4R^5SiO)_n$ is selected from the group comprising 1,1,3,3,5,5-hexamethyl-cyclotrisiloxane, 1,1,3,3,5,5,7,7-octamethyl-cyclotetrasiloxane, 1,1,3,3,5,5,7,7,9,9-decamethyl-cyclopentasiloxane, 1,1,3,3,5,5,7,7,9,9,11,11-dodecamethyl-cyclohexasiloxane.

11. Process according to claim 10, wherein said cyclosiloxane of formula $(R^4R^5SiO)_n$ is 1,1,3,3,5,5-hexamethyl-cyclotrisiloxane.

12. Process according to claim 1, wherein said suitable catalyst for the reaction is an acidic catalyst.

13. Process according to claim 12, wherein said catalyst is selected from the group comprising hydrochloric acid, acetic acid, nitric acid, sulfuric acid, trifluoromethanesulfonic acid, trifluoracetic acid, acetic acid, a strongly acidic ion exchange resin of the sulfonic type, $ZnCl_2$, $BeCl_2$, $TiCl_4$, $SnCl_4$, $FeCl_3$, $FeCl_2$, $SbCl_5$, $AlCl_3$ and other metal halides.

14. Process according to claim 13, wherein said catalyst is $ZnCl_2$.

15. Process according to claim 13, wherein said catalyst is trifluoromethanesulfonic acid.

16. Process according to claim 13, wherein said catalyst is a strongly acidic ion exchange resin of the sulfonic type.

17. Process according to claim 12, further comprising the step of neutralising the acidic catalyst with a base.

18. Process according to claim 17, wherein said base is selected from the group comprising triethylamine, diethylamine, tributylamine, hexamethyldisilazane N-methylmorpholine, diisopropylethylamine, dicyclohexylamine, N-methylpiperidine, pyridine, 4-pyrrolidinopyridine, picoline, 4-(N,N-dimethylamino) pyridine, 2,6-di(t-butyl)-4-methylpyridine, quinoline, N,N-dimethylaniline and N,N-diethylaniline and the like.

19. Process according to claim 18, wherein said base is triethylamine.

20. Process according to claim 1, wherein the step of reacting the cyclosiloxane of formula $(R^4R^5SiO)_n$ with the unsaturated organosilylated carboxylate of formula (II) or a copolymer, or a polymer thereof is optionally performed in the presence of a suitable solvent.

21. Process according to claim 20, wherein said solvent is a nonpolar inert solvent selected from the group comprising benzene, toluene, xylene, mesitylene, ethylbenzene, pentane, hexane, cyclohexane, heprane, octane, decane, decahydronaphthalene, diethyl ether, diisopropyl ether, diisopropyl ether, diisobutyl ether, or mixtures thereof.

22. Process according to claim 1, wherein said reaction is performed at a temperature selected in the range of 20 to 150° C.

23. Process according to claim 1, wherein said reaction is performed at room temperature.

24. Process according to claim 1, wherein n represents a number of dihydrocarbylsiloxane units from 3 to 8.

25. Process according to claim 1, wherein n represents a number of dihydrocarbylsiloxane units from 3 to 6.

26. Process according to claim 1, wherein said reaction is performed at a temperature selected in the range of 50 to 120° C.

27. Process according to claim 1, wherein said reaction is performed at a temperature selected in the range of 90 to 110° C.

* * * * *

UNITED STATES PATENT AND TRADEMARK OFFICE
CERTIFICATE OF CORRECTION

PATENT NO. : 7,595,370 B2  Page 1 of 1
APPLICATION NO. : 10/520636
DATED : September 29, 2009
INVENTOR(S) : Plehiers et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1029 days.

Signed and Sealed this

Twenty-eighth Day of September, 2010

David J. Kappos
*Director of the United States Patent and Trademark Office*